(12) United States Patent
Qian

(10) Patent No.: US 6,353,041 B1
(45) Date of Patent: Mar. 5, 2002

(54) DENTAL COMPOSITIONS

(75) Inventor: Xuejun Qian, Foothill Ranch, CA (US)

(73) Assignee: Kerr Corporation, Orange, CA (US)

( * ) Notice: Subject to any disclaimer, the term of this patent is extended or adjusted under 35 U.S.C. 154(b) by 0 days.

(21) Appl. No.: 09/425,477

(22) Filed: Oct. 22, 1999

(51) Int. Cl.$^7$ ................................................ A61K 6/08
(52) U.S. Cl. ................ 523/116; 433/228.1; 523/117; 523/118
(58) Field of Search ................ 523/116, 117, 523/118; 433/228.1

(56) References Cited

U.S. PATENT DOCUMENTS

| | | | |
|---|---|---|---|
| 4,184,879 A | 1/1980 | Ducos et al. | 103/35 |
| 4,507,458 A | 3/1985 | Shiraki et al. | 528/49 |
| 4,741,596 A | 5/1988 | Broer et al. | 350/96.34 |
| 4,798,852 A | 1/1989 | Zimmerman et al. | 522/96 |
| 4,813,876 A | 3/1989 | Wang | 433/224 |
| 4,931,096 A | 6/1990 | Fujisawa et al. | 106/35 |
| 4,936,775 A | 6/1990 | Bennett | 433/220 |
| 4,950,697 A | 8/1990 | Chang et al. | 523/116 |
| 5,146,531 A | 9/1992 | Shustack | 385/128 |
| 5,228,907 A | 7/1993 | Eppinger et al. | 106/35 |
| 5,326,264 A | 7/1994 | Kasem | 433/224 |
| 5,362,769 A * | 11/1994 | Walter et al. | 523/118 |
| RE35,264 E | 6/1996 | Bennett | 433/220 |
| 5,571,570 A | 11/1996 | Lake | 427/494 |
| 5,624,976 A | 4/1997 | Klee | 523/116 |
| 5,646,197 A | 7/1997 | Martin | 523/118 |
| 5,648,403 A | 7/1997 | Martin | 523/117 |
| 5,683,249 A | 11/1997 | Ibsen et al. | 433/201.1 |
| 5,730,601 A * | 3/1998 | Bowman et al. | 523/118 |
| 5,814,682 A | 9/1998 | Rusin et al. | 523/116 |
| 6,071,528 A * | 6/2000 | Jensen | 424/427 |
| 6,133,339 A * | 10/2000 | Xie et al. | 523/116 |
| 6,149,655 A * | 11/2000 | Constantz et al. | 606/94 |

FOREIGN PATENT DOCUMENTS

| | | | |
|---|---|---|---|
| EP | 0 064 845 A2 | 11/1982 | A61C/5/04 |
| EP | 0 630 640 A1 | 12/1994 | A61K/6/083 |
| EP | 0 630 641 A | 12/1994 | A61K/6/083 |
| EP | 0 988 851 A2 | 3/2000 | A61K/6/08 |
| WO | WO 93/10176 | 5/1993 | C08K/5/04 |

OTHER PUBLICATIONS

Tatsujiro, F. and Yoji, I., *Cytotoxicity Test of a New Experimental Sealer and Various Commercial Materials for Root Canal Filling*, Japanese Journal of Conservative Dentistry, vol. 35, No. 5, pp. 1252–1257 (1992) Abstract.

Tatsujiro, F. and Yoji, I., *Preparation and Properties of New Root Canal Filling Material with Adhesiveness to Tooth*, Japanese Journal of Conservative Dentistry, vol. 35, No. 1, pp. 232–239 (1992) Abstract.

Tatsujiro, Funishima, *Study on Resin Type Root Canalk Filling Material with Adhesiveness to Tooth*, Japanese Journal of Conservative Dentistry, vol. 35, No. 6, pp. 1513–1522 (1992) Abstract.

* cited by examiner

*Primary Examiner*—Paul R. Michl
(74) *Attorney, Agent, or Firm*—Wood, Herron & Evans, LLP

(57) ABSTRACT

A two part composition for sealing and/or filling root canals. One or more elastomeric (meth)acrylate oligomers are mixed with one or more diluent comonomers, one or more radiopaque fillers and one or more polymerization initiator systems. One or more antimicrobial agents may also be included in the composition. The components are mixed, undergo a setting reaction and are subsequently cured. In use, the composition is easily removed from the tooth structure if rework is needed, yet provides a tight and effective seal in the root canal. The composition also has a desirable flowable consistency and exhibits good adhesiveness with a tooth substrate.

31 Claims, No Drawings

DENTAL COMPOSITIONS

FIELD OF THE INVENTION

The invention is directed to dental compositions, particularly for filling and sealing a root canal.

BACKGROUND OF THE INVENTION

When treating an infected root canal, the infected dentin is removed and the pulp and canal are then cleaned and disinfected. The disinfected canal is shaped and filled with a filling material that is cemented with a sealer.

The desirable properties for a root canal filling material include ease of removal from the canal if rework is needed, ease of manipulation with ample working time, dimensional stability (minimal shrinkage or change of form after insertion), ability to seal the canal laterally and apically (conforming and adapting to the various shapes and contours of individual canals), lack of irritation to periapical tissues, inertness and insolubility in tissue fluids. A desirable root canal filling material also provides bacteriostatic properties and is radiopaque.

Gutta percha is currently the root canal filling material of choice because, with careful manipulation, gutta percha can fulfill many of the above requirements. Gutta percha is available in cone shapes with different sizes. Its composition is gutta percha (a natural rubber) as a thermoplastic resin matrix, zinc oxide as a filler, one or more barium- or strontium-containing compounds as a filler and radiopacifier, waxes or resins, pigments and plasticizers.

The most common sealing material is a zinc oxide-eugenol type in a powder and liquid configuration. The powder is composed of zinc oxide and other additives such as a radiopacifier and colloidal silica, and the liquid is composed of eugenol and other resinous material and additives such as a plasticizer. When the powder and liquid are mixed in the presence of moisture, zinc oxide and eugenol undergo a setting reaction and the pasty material slowly becomes a solid. The sealer is used to fill any gaps between the gutta percha cones as well as in the lateral canal branches. The gutta percha filler needs to be softened by heat and then condensed into the canal, forcing the sealer to have an intimate contact with the canal wall and to fill the lateral canal branches.

The above method of filling and sealing the canal is, however, rather complicated. Separate sealing and filling materials are used. The gutta percha cone needs to be softened by heat in order to compact it inside the canal, and has a rather limited working time once the heat source is removed. Also, there are some other drawbacks associated with both materials. The zinc oxide-eugenol mixture is brittle, fragile, not very coherent and can easily disintegrate under a small stress. The zinc oxide-eugenol sealer is quite soluble in oral fluids, slowly dissolving away and leaving gaps between the filling material and the canal wall. Bacteria or other microorganisms can multiply in such gaps, causing infection and inflammation inside the canal and surrounding tissues. The gutta percha filling materials are quite hard and difficult to remove whenever rework is needed; removal often requires the application of a toxic organic solvent to soften the material. The gutta percha filling materials are also quite brittle and prone to breakage during insertion into root canals due to their intricate shape.

Therefore, there is a need to improve existing canal filling and/or sealing materials.

SUMMARY OF THE INVENTION

The invention is directed to a dental composition that may be used as a root canal sealing material, a root canal filling material, or a root canal filling and sealing material in one. The composition may be a two-part system of a powder/liquid or a paste/paste. The inventive composition provides a tight and effective seal in the root canal, yet is easily removed from the tooth structure if rework is needed. The composition also has a desirable flowable consistency and exhibits good adhesiveness with a tooth substrate.

The composition has at least one elastomeric acrylate (acrylate, as used herein, means either acrylate or methacrylate and may be abbreviated as (meth)acrylate) oligomer, at least one diluent comonomer that has at least one ethylenically unsaturated group, at least one filler and at least one polymerization initiator system.

The elastomeric (meth)acrylate oligomer may be a urethane (meth)acrylate oligomer or a polyalkyleneglycol (meth)acrylate oligomer. The concentration of the elastomeric (meth)acrylate oligomer may be 0.5–50% by weight. The filler may be inorganic metal, salt, inorganic oxide, silicate, aluminosilicate, aluminoborosilicate, fluoroaluminosilicate, colloidal silica, precipitated silica, polymeric solid, or mixtures of the above. The polymerization initiator system may be a redox initiator system.

The composition may optionally contain one or more antimicrobial agents. The antimicrobial agent may be, for example, benzalkonium chloride, iodoform, eugenol, zinc oxide, triclosan, butyl parahydroxybenzoate or mixtures of the above. The inventive compositions may also contain calcium hydroxide, one or more adhesion promoters, a plasticizer, and a wetting agent or surfactant.

The invention also includes a method of sealing and/or filling a root canal by preparing the inventive composition and providing the prepared composition to fill and/or seal a root canal.

These and other embodiments of the inventive composition will be apparent in light of the following detailed description and examples.

DETAILED DESCRIPTION

A two part composition for use in filling and sealing root canals is disclosed. One or more elastomeric acrylate (acrylate, as used herein, means either acrylate or methacrylate and may be abbreviated as (meth)acrylate) oligomers are mixed with one or more diluent comonomers, one or more radiopaque fillers and one or more polymerization or curing initiator systems. In one embodiment, one or more antimicrobial agents may be included in the composition. The elastomeric (meth)acrylate oligomer provides soft or elastomeric materials upon setting. The diluent comonomer controls the viscosity and optimizes the physical properties of the composition. The radiopaque filler facilitates detection of gaps or voids. The optional antimicrobial agent controls infection.

In use, the components are mixed and undergo a setting reaction. The set components are subsequently cured. The composition, upon curing, has a low modulus and is therefore flexible, which facilitates easy removal from the tooth structure should dental rework be needed. The composition exhibits only a small amount of shrinkage upon curing and may even slightly expand upon water absorption. This produces a tight and effective seal in the root canal. The composition also has a desirable flowable consistency and exhibits good adhesiveness with a tooth substrate.

Thus, the composition is an endodontic material that can function as a sealing and/or a filling material, and thereby eliminate the need for separate filling and sealing materials.

The invention is also directed to a root canal sealing and/or filling material that, when hardened, remains soft and flexible so that it can be easily removed from the canal if rework becomes necessary. This is achieved by utilizing a special (meth)acrylate oligomer that is flexible upon hardening. The composition, when applied, does not require the application of heat to compact it inside the canal.

The composition is antibacterial in some embodiments, is radiopaque, exhibits minimal volumetric shrinkage during curing, is dimensionally stable in oral fluids and has limited solubility in oral fluids. It has good adhesive properties and adapts well to canal walls and irregularities.

The root canal sealing and/or filling compositions of the invention comprise one or more elastomeric (meth)acrylate oligomers that have a low elastic modulus and that remain soft and flexible upon curing through free radical polymerization. "Acrylate" as used herein is a monomer, oligomer or prepolymer that contains one or more acrylate or methacrylate functional groups and may be abbreviated as (meth) acrylate. "Elastomeric" as used herein means that the (meth) acrylate oligomer, after polymerization, has a rather low elastic modulus and is quite elastic and flexible. Preferred elastomeric (meth)acrylate oligomers are urethane (meth) acrylate oligomers and a polyalkyleneglycol (meth)acrylate oligomer.

The urethane (meth)acrylate oligomer may be (1) the reaction product between one or more polyols (polyether polyols, polyester polyols, or polyether/polyester polyols), one or more organic diisocyanates, and one or more monohydric (meth)acrylate (acrylate monomer with one reactive hydroxyl group); and/or (2) the reaction product between one or more polyols (polyether polyols, polyester polyols, or polyether/polyester polyols), one or more organic diisocyanates, and one or more isocyanatoalkyl (meth) acrylates (acrylate monomers with one reactive isocyanate group). The polyalkyleneglycol (meth)acrylate oligomer is an acrylate ester of a polyalkylene glycol.

The root canal sealing and/or filling compositions may also include other ingredients such as an (meth)acrylate comonomer, a curing initiator, an antibacterial agent, a radiopaque filler, an adhesion promoter and a plasticizer. Compositions containing the disclosed (meth)acrylate oligomer would yield a soft and elastic polymeric material upon curing.

This invention discloses a novel endodontic sealing material that can be used as a sealing material and/or filling material. This new endodontic obturation material offers the following desirable characteristics. It has a low elastic modulus after setting and remains elastic and flexible so it can be easily removed if rework is necessary, offering easy manipulation with ample working time and an easy root canal procedure. It has good adhesive properties allowing it to adhere well to tooth structures and minimize gap formation. Upon setting, it exhibits minimal shrinkage and therefore can create excellent contacts with root canal walls, minimizing gap formation. It has excellent dimensional stability and minimal solubility in water. Therefore, it can maintain a good seal and contact with tooth structures, ensuring long lasting sealing, and it has the ability to adapt to intricate canal geometries. It exhibits excellent antibacterial properties in some embodiments and prevents microorganism growth and infection. It exhibits good radiopacity for easy detection of gaps and voids.

The endodontic sealing and/or filling material utilizes (meth)acrylate monomers/oligomers which undergo free-radical polymerization using a polymerization initiator system such as redox initiator system. The composition of this endodontic filling/sealing material comprises the following components: (a) one or more elastomeric (meth)acrylate oligomers, such as an elastomeric urethane (meth)acrylate oligomer or an elastomeric polyalkyleneglycol (meth) acrylate oligomer, (b) one or more (meth)acrylate comonomers, (c) one or more fillers, and (d) a polymerization initiator system.

Component (a), the elastomeric (meth)acrylate oligomer, exhibits a low elastic modulus and remains flexible upon curing. As a root canal sealing and/or filling material, this elastic and flexible property allows the cured material to be removed with little difficulty if rework is needed at a later time. Also, the uncured paste is quite fluid and can be easily condensed into the canal and conform to the canal geometries without the need to apply heat, as in the case with conventional gutta percha cones.

In one embodiment, the first preferred elastomeric (meth) acrylate oligomer is a urethane (meth)acrylate oligomer. There are two types of urethane (meth)acrylate oligomers which may be used. The first type of elastomeric urethane (meth)acrylate oligomer (see Structure I below) is a reaction product between one or more polyols (selected from polyether polyols, polyester polyols, or polyether/polyester polyols), one or more organic diisocyanates, and one or more monohydric (meth)acrylates (acrylate monomers with one reactive hydroxyl group). Examples of monohydric (meth)acrylate include, but are not limited to, 2-hydroxyethyl acrylate, 2-hydroxyethyl methacrylate, 2-hydroxypropyl acrylate, 2-hydroxypropyl methacrylate, 2-hydroxy-2'-ethoxyethyl acrylate, 2-hydroxy-2'-ethoxyethyl methacrylate and mixtures thereof.

The second type of elastomeric urethane (meth)acrylate oligomer (see Structure II below) is a reaction product between one or more polyols (selected from polyether polyols, polyester polyols, or polyether/polyester polyols), one or more organic diisocyanates, and one or more isocyanatoalkyl (meth)acrylates (acrylate monomers with one reactive isocyanate group).

Structure I (Urethane Acrylate Oligomer Type 1)

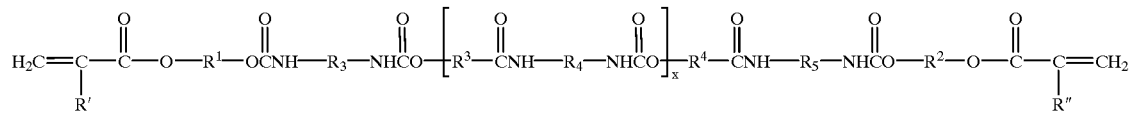

Structure II (Urethane Acrylate Oligomer Type 2)

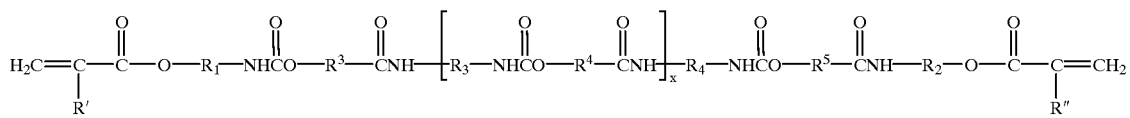

Where
- x=0–30;
- R', R''=H or CH$_3$; R' and R'' may be the same or different;
- R$_1$, R$_2$=—C$_n$H$_{2n}$—; n=1–14; R$_1$ and R$_2$ is an aliphatic group and may be the same or different;
- R$_3$, R$_4$ and R$_5$ are the bivalent radicals of an organic diisocyanate compound and may be the same or different;
- R$^1$, R$^2$=—(G—O)$_y$—G ; y=0–40; R$^1$, R$^2$ may be the same or different;
- R$^3$, R$^4$, R$^5$ may be the same or different, and is selected from the following structures:

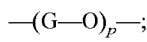

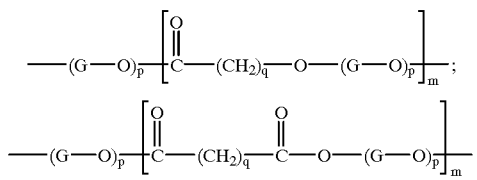

Where p, q=1–40; m=1–30; and G in R$^1$, R$^2$, R$^3$, R$^4$ and R$^5$ is selected from the following structures:

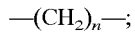

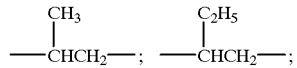

n=1–12.

The preferred R$_1$, R$_2$ group above is either —CH$_2$CH$_2$—, —CH$_2$CH$_2$CH$_2$—or —CH$_2$CH$_2$CH$_2$CH$_2$—. Examples of useful bivalent radicals of an organic diisocyanate compound (i.e. R$_3$, R$_4$, and R$_5$ above) include, but are not limited to, 1,4-tetramethylene diisocyanate; 1,5-pentamethylene diisocyanate; 1,6-hexamethylene diisocyanate; 1,7-heptamethylene diisocyanate; 1,8-octamethylene diisocyanate; 1,9-nonamethylene diisocyanate; 1,10-decamethylene diisocyanate; 2,4,4-trimethyl- 1,6-hexamethylene diisocyanate; 2,2,4-trimethyl-1,6-hexamethylene diisocyanate; 2,2,4-trimethyl-1,5-pentamethylene diisocyanate; toluene diisocyanate; diphenylmethane-4,4'-diisocyanate; isophorone diisocyanate; dicyclohexylmethane-4,4'diisocyanate; 1,4-cyclohexyl diisocyanate; and 1,3-cyclohexyl diisocyanate. The preferred diisocyanates are 1,6-hexamethylene diisocyanate; 2,4,4-trimethyl-1,6-hexamethylene diisocyanate; 2,2,4-trimethyl- 1,6-hexamethylene diisocyanate; toluene diisocyanate; diphenylmethane-4,4'-diisocyanate and isophorone diisocyanate.

The elastomeric urethane (meth)acrylate oligomers with an average molecular weight of 500 to 50,000 are preferred. The more preferred average molecular weight is 1,000 to 10,000. The most preferred average molecular weight is 1,500 to 5,000. The urethane (meth)acrylate oligomer can have one or more acrylate or methacrylate functional groups.

There are several commercially available elastomeric urethane (meth)acrylate oligomers that may be used in the current invention. Examples of those oligomers include Ebecryl® series resins (e.g. Ebecryl® 270, 230, 810, USB Radcure Corporation, Smyrna, Ga.) and CN series resins (e.g. CN964, CN966, CN970, Sartomer Co., Exton, Pa.).

In another embodiment, the elastomeric (meth)acrylate oligomer is a polyalkyleneglycol acrylate oligomer. The polyalkyleneglycol (meth)acrylate can contain one or more acrylate or methacrylate groups. The elastomeric polyalkyleneglycol (meth)acrylate has the following structure:

Structure III (Polyalkyleneglycol Acrylate Oligomer)

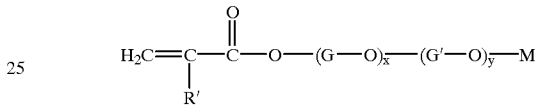

Where
- x=0–100; y=1–100, and x+y=6–100
- R'=H or CH$_3$;
- G and G' are selected from the following structures:

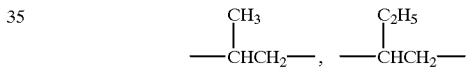

where m=1–12;

M is selected from following structures:
H, C$_n$H$_{2n+1}$ (alkyl group),

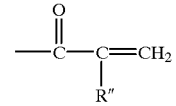

where
- n=1–8;
- R''=H or CH$_3$.

Suitable polyalkyleneglycol (meth)acrylate oligomers useful for the present invention include, but are not limited to, polyethyleneglycol mono- or di-(meth)acrylate, polypropyleneglycol mono- or di-(meth)acrylate, polyisopropyleneglycol mono- or di-(meth)acrylate, and polytetramethyleneglycol mono- or di-(meth)acrylate. The preferred molecular weight for the polyalkyleneglycol (meth)acrylate oligomer is in the range of 400–5,000, the more preferred molecular weight is in the range of 500–3,000 and the most preferred molecular weight is in the range of 600–2,500.

The above elastomeric urethane (meth)acrylate oligomer or polyalkyleneglycol (meth)acrylate oligomer can be used alone or can be used as a mixture of several different oligomers. They are usually quite viscous and often require the incorporation of other low viscosity diluent comonomers to reduce the viscosity. This makes it easy to formulate the resin with other ingredients and makes the paste easy to manipulate. Other comonomers can also be used to increase the polymerization rate of the elastomeric (meth)acrylate oligomer that usually has a slow cure response. The comonomer has at least one ethylenically unsaturated group and can copolymerize with the elastomeric (meth)acrylate oligomer. Examples of ethylenically unsaturated groups include vinyl, acrylate and methacrylate groups. Preferred ethylenically unsaturated groups are acrylate and methacrylate groups. Examples of comonomers include, but are not limited to, hydroxyethyl (meth)acrylate, hydroxypropyl (meth)acrylate, hydroxybutyl (meth)acrylate, glycerol di(meth)acrylate, glycerol mono(meth)acrylate, methyl (meth)acrylate, ethyl (meth)acrylate, propyl (meth)acrylate, butyl (meth)acrylate, hexyl (meth)acrylate, octyl (meth) acrylate, lauryl (meth)acrylate, decyl (meth)acrylate, tridecyl (meth)acrylate, 2-ethoxyethyl (meth)acrylate, 2'-ethoxy-2-ethoxyethyl (meth) acrylate, ethyleneglycol di(meth) acrylate, diethyleneglycol di(meth)acrylate, triethyleneglycol di(meth)acrylate, tetraethyleneglycol di(meth)acrylate, polyethyleneglycol (PEG) mono- or di-(meth)acrylate with the molecular weight of PEG ranging from 160 to 400, polypropyleneglycol (PPG) mono- or di-(meth)acrylate with the molecular weight of PPG ranging from 50 to 400, polyisopropyleneglycol mono- or di- (meth) acrylate with the molecular weight of polyisopropyleneglycol ranging from 50 to 400, polytetramethyleneglycol mono- or di- (meth)acrylate with the molecular weight of polytetramethyleneglycol ranging from 60 to 400, hexanediol di(meth)acrylate, trimethylolpropane tri(meth)acrylate, UDMA (reaction product of 2-hydroxyethyl methacrylate with 2,4,4-trimethylhexane diisocyanate), ethoxylated bisphenol A di(meth)acrylate, tetrahydrofurfuryl (meth) acrylate, or mixtures thereof.

The preferred concentration of the elastomeric (meth) acrylate oligomer is about 0.5–50% by weight, the more preferred concentration is about 1–40% by weight, and the most preferred concentration is about 2–30% by weight.

An inorganic filler is used to provide enhancement to the mechanical and rheological properties of the composition, to increase radiopacity for easy detection of gaps or voids, and to reduce polymerization shrinkage. Examples of fillers include inorganic metal, salt, oxide, silicate, aluminosilicate, aluminoborosilicate, fluoroaluminosilicate, colloidal silica, precipitated silica, polymeric solid, and mixtures thereof. The preferred inorganic fillers for increased x-ray contrast include metal, silicate, aluminosilicate, salt and oxide containing elements of high atomic number such as strontium, bismuth, tungsten, barium, ytterbium, yttrium, etc., with examples including barium sulfate, silver, strontium fluoride, barium fluoride, ytterbium fluoride, yttrium fluoride, barium tungstate, zinc oxide, bismuth(III) oxide, bismuth subcarbonate $(BiO)_2CO_3$, bariumaluminosilicate, bariumalumino borosilicate, strontium-aluminosilicate, bariumaluminofluorosilicate, strontiumaluminofluorosilicate, zincaluminosilicate, etc. Fumed silica, colloidal silica, or precipitated silica can also be incorporated to improve the dispersion of the filler, as well as the rheological and handling properties of the material.

The curing or hardening of the resin is through free-radical polymerization of the ethylenically unsaturated group, e.g., the (meth)acrylate group. A redox initiator system that comprises at least one reducing agent and at least one oxidizing agent may be used. Among preferred reducing agents are a tertiary amine, an organic compound containing the —$SO_2M$ group (where M is H or alkali metal ion), and ascorbic acid and its derivatives. The most preferred reducing agent is either N,N-dihydroxyethyl p-toluidine, N,N-dimethyl p-toluidine, N,N-dimethylaminophenylethyl alcohol, N,N-dimethylaminophenylacetic acid, benzenesulfinic acid, toluenesulfinic acid, sodium benzenesulfinate, potassium benzenesulfinate, sodium toluenesulfinate or potassium toluenesulfinate. The preferred oxidizing agent is an organic peroxide. The most preferred peroxide is either benzoyl peroxide, hydrogen peroxide, di-t-butyl peroxide or t-butyl hydrogen peroxide. The concentration of the initiators should be in the range of about 0.01–3.0% by weight with a preferred concentration range of about 0.05–2.0%.

In one embodiment the composition is a two-part liquid/powder or paste/paste system with each part containing a component of the redox initiator system (either reducing agents or oxidizing agents). When the two parts are mixed, the (meth)acrylate resins of the mixed paste start to polymerize and the paste starts to harden. The working time and the set time can be adjusted by varying the concentration of the initiators and the stabilizers. The preferred stabilizers include 4-methoxyphenol and 2,6-di-(t-butyl)-4-methylphenol. When the configuration is a powder/liquid combination, the liquid mixture is formed by mixing all the (meth)acrylate resins (including monomers, oligomers and prepolymers) and all the additives (initiator, stabilizer, antibacterial agent, plasticizer, wetting agent) that are soluble in the (meth)acrylate resin mixture. The powder mixture is formed by blending all the fillers with the initiator (either the reducing or the oxidizing agent) together along with any solid additives. The paste mixture is formed by mixing the liquid mixture with powders.

In some embodiments of the present invention, the composition can also include one or more adhesion promoters to improve adhesion to the tooth structure. Preferred adhesion promoters include organic compounds containing at least one of the following hydrophilic groups, either a hydroxyl group or an acidic group selected from
—COOH;

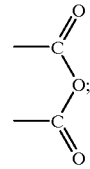

—$SO_3H$; —$SO_2H$;

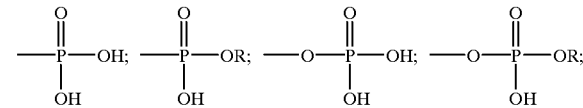

Where R is an alkyl or aryl group.

The most preferred adhesion promoter also contains at least one ethylenically unsaturated group so that it can copolymerize with other monomers or oligomers. Examples of adhesion promoters include, but are not limited to, glycerin, polyethyleneglycol, hydroxyethyl (meth)acrylate, hydroxypropyl (meth)acrylate, glycerol di(meth)acrylate, glycerol mono(meth)acrylate, glyceroldi(meth)acrylate phosphate, (meth)acryloyloxydecyl phosphate, 4-(meth) acryloxyethyl trimellitic anhydride, (meth)acryloxyethyl maleate, phthalic acid monoethyl(meth)acrylate, a reaction product of pyromellitic dianhydride with hydroxyethyl (meth)acrylate, a reaction product of pyromellitic dianhydride with glyceroldi(meth)acrylate, or mixtures thereof.

In another embodiment, the composition also includes a plasticizer to further increase flexibility. Examples of plasticizers include, but are not limited to, dibutylphthalate, dibutoxyethoxyethyl adipate, dibutoxyethoxylethyl formal, etc.

In yet another embodiment, the composition contains one or more antimicrobial agents. Examples of antimicrobial agents include, but are not limited to, benzalkonium chloride, iodoform, eugenol, zinc oxide, triclosan, butyl parahydroxybenzoate and mixtures thereof. Calcium hydroxide has a pharmaceutical effect, and is said to promote the growth of secondary dentin. When incorporated in the current compositions, similar effects are expected.

In other embodiments, the compositions of the present invention may also contain a wetting agent or surfactant to improve the wetting or dispersion of the inorganic filler in the resin.

Consistency Measurement

The viscosity of the paste is roughly characterized by a consistency measurement. One (1.00) gram of paste is placed onto a 2"×3" glass slide. A second 2"×3" glass slide and an additional mass with a total weight of 120±2 g was gently placed over the paste. After exactly 10 minutes, the weight was removed and the minor and major diameter of the slumped paste was immediately measured in centimeters. The consistency value is the average of the two diameters. A paste of higher viscosity would usually yield a smaller consistency value.

Elastic Modulus Measurement

The elastic modulus was measured from the slope of the initial linear region on the stress-strain curve during the flexural testing. Flexural testing is a three-point bending setup using specimens with a rectangular bar geometry. The base paste contains the reducing agent, e.g., a tertiary amine, of the redox initiator system, and the catalyst paste contains the oxidizing agent, e.g., an organic peroxide, of the redox initiator system. Five specimens were prepared for each pair of base/catalyst sealer formulas. A split mold made of stainless steel with an inside dimension of 3 mm×3 mm×30 mm was used for fabricating the specimens. A Mylar sheet was placed on a 2"×3" glass slide and then the assembled split mold was placed on the Mylar sheet. Equal amounts of base and catalyst pastes were mixed with a spatula for about 30 sec. The mixed paste was slightly overfilled into the mold and another Mylar sheet was placed on the top. Another 2"×3" glass slide was placed on top of the Mylar sheet and some pressure was applied to remove excess paste from the mold. The paste was allowed to set and harden for about one hour in the mold. The specimen was then carefully removed from the mold and any excess material or flashes from the specimen were also removed. The specimen was placed in a container filled with water and stored in a 37° C. oven for 24 h before testing.

Testing was performed on an Instron Testing Machine (Model 4467, Instron Corp.). A three point bending apparatus with a support span of 2 mm was used. Testing was conducted with a crosshead speed of 5 mm/min. The force and displacement were digitally collected by a computer loaded with an Instron IX software package. The modulus was calculated automatically by the software.

Shore "A" Hardness Measurement

Equal amounts of base and catalyst pastes were mixed. The mixed paste was filled into a 10.0 mm×2.0 mm (diameter×height) stainless steel mold resting on a 1"×3" glass slide. The mold was overfilled, an 18 mm×18 mm cover glass slip was placed on the top and the assembly was pressurized with a 1"×3" glass slide to remove excess paste. The paste was allowed to set and harden for about one h and then the specimens were removed from the mold. A Shore "A" Durameter (Shore Instrument Co.) was used to measure hardness.

In all the following examples for making a paste, a homogeneous unfilled resin mixture was made first by mixing all resins with initiators and additives. The resin mixture was then further blended together with appropriate fillers including colloidal silicas.

The invention will be further appreciated in light of the following examples. In the examples the following materials were used:

| | |
|---|---|
| A-174 | γ-methacryloyloxypropyltrimethoxysilane |
| BaAlBSi filler | bariumaluminoborosilicate filler that has a mean particle size of 1.0 μm and the following composition (mole %): $SiO_2$ (67), BaO (16.4), $B_2O_3$ (10), $Al_2O_3$ (6.6) |
| BAC | benzalkonium chloride |
| BHT | 2,6-di-(tert-butyl)-4-methylphenol |
| Bis-GMA | 2,2-bis[4-(2-hydroxy-3-methacryloylpropoxy)-phenyl]-propane |
| BPB | butyl para-hydroxybenzoate |
| BPO | benzoyl peroxide |
| CN966 | a urethane diacrylate oligomer based on polyester polyol (Sartomer Co.) |
| Ebecryl ® 270 | urethane acrylate oligomer (UCB Radcure Inc.) |
| EBPADMA | ethoxylated bisphenol A dimethacrylate |
| EOEOEA | 2-(2-ethoxyethoxy)ethyl acrylate |
| DHEPT | N,N-dihydroxyethyl-p-toluidine |
| GPDM | glycerylphosphate dimethacrylate |
| HEMA | 2-hydroxyethyl methacrylate |
| MEMA | methacryloyloxyethyl maleate |
| OX-50 | fumed silica or colloidal silica (Degussa) |
| PEG-600 DMA | poly(ethyleneglycol) dimethacrylate (average molecular weight of PEG is 600) |
| R-972 | surface treated fumed silica or colloidal silica (Degussa) |
| SR604 | polypropyleneglycol monomethacrylate with a molecular weight of 405 (Sartomer Co.) |
| TEGDMA | triethyleneglycol dimethacrylate |
| TS-530 | surface treated fumed silica or colloidal silica (Cabot Corp.) |

EXAMPLE 1

A) Base Resin mixture composition

| Ingredients | Parts by Weight |
|---|---|
| HEMA | 8.00 |
| TEGDMA | 15.00 |
| CN966 | 31.18 |
| EOEOEA | 3.46 |
| SR604 | 30.00 |
| Dibutyl phthalate | 10.00 |
| BAC | 1.00 |
| DHEPT | 1.30 |
| BHT | 0.06 |

B) Catalyst Resin mixture composition

| Ingredients | Parts by Weight |
|---|---|
| HEMA | 8.00 |
| MEMA | 5.00 |
| TEGDMA | 15.00 |
| CN966 | 30.74 |
| EOEOEA | 3.42 |
| SR604 | 25.00 |

-continued

B) Catalyst Resin mixture composition

| Ingredients | Parts by Weight |
|---|---|
| Dibutyl phthalate | 10.00 |
| BAC | 1.00 |
| BPO | 1.70 |
| BHT | 0.14 |

C) Base and Catalyst Paste composition (in parts by weight)

| Ingredients | Base Paste (wt. %) | Catalyst Paste (wt %) |
|---|---|---|
| Base Resin Mixture (A) | 52.0 | — |
| Catalyst Resin Mixture (B) | — | 52.0 |
| Zinc Oxide | 15.0 | 15.0 |
| Barium Sulphate | 11.0 | 11.0 |
| BaAlBSi Filler[1] | 19.0 | 19.0 |
| OX-50[1] | 1.0 | 1.0 |
| TS-530 | 2.0 | 2.0 |

[1]Both BaAlBSi filler and OX-50 fumed silica were surface treated with γ-methacryloyloxypropyltrimethoxysilane.

The Base Paste had a consistency value of 4.5 cm and the Catalyst Paste had a consistency value of 4.0 cm. The Mixed Base and Catalyst Paste had a working time of 24 min and set time of 43 min. The set material had a Shore A hardness of 82, a flexural modulus of 8±1 MPa and a flexural strength of 1.4±0.2 MPa.

EXAMPLE 2

A) Base Resin mixture composition

| Ingredients | Parts by weight |
|---|---|
| HEMA | 10.0 |
| TEGDMA | 10.0 |
| Ebecryl ® 270 | 32.64 |
| PEG-600 DMA | 20.0 |
| SR604 | 15.0 |
| Dibutoxyethoxyethyl adipate | 10.0 |
| BAC | 1.00 |
| DHEPT | 1.30 |
| BHT | 0.06 |

B) Catalyst Resin mixture composition

| Ingredients | Parts by weight |
|---|---|
| HEMA | 6.0 |
| GPDM | 6.0 |
| TEGDMA | 10.0 |
| Ebecryl ® 270 | 30.16 |
| PEG-600 DMA | 20.0 |
| SR604 | 15.0 |
| Dibutoxyethoxyethyl adipate | 10.0 |
| BAC | 1.00 |
| BPO | 1.70 |
| BHT | 0.14 |

C) Base and Catalyst Pastes compositions (in parts by weight)

| Ingredients | Base Paste (wt. %) | Catalyst Paste (wt %) |
|---|---|---|
| Base Resin Mixture (A) | 48.0 | — |
| Catalyst Resin Mixture (B) | — | 48.0 |
| Zinc Oxide | 10.0 | 10.0 |
| Barium Sulphate | 30.0 | 30.0 |
| BaAlBSi Filler[1] | 9.5 | 9.5 |
| OX-50[1] | 0.5 | 0.5 |
| Aerosol R972 | 2.0 | 2.0 |

[1]Both BaAlBSi filler and OX-50 fumed silica were surface treated with γ-methacryloyloxypropyltrimethoxysilane.

The Base Paste had a consistency value of 4.6 cm and the Catalyst Paste had a consistency value of 5.8 cm. The mixed Base and Catalyst Paste had a working time of 21 min and set time of 30 min. The set material had a Shore A hardness of 87, a flexural modulus of 45±11 MPa and a flexural strength of 7.2±0.8 MPa.

Comparative Example

This example is for comparison only, not in accordance with the current invention.

A) Base Resin mixture composition

| Ingredients | Parts by weight |
|---|---|
| HEMA | 8.0 |
| TEGDMA | 40.0 |
| BisGMA | 30.14 |
| EBPADMA | 20.0 |
| BPB | 0.5 |
| DHEPT | 1.3 |
| BHT | 0.06 |

B) Catalyst Resin mixture composition

| Ingredients | Parts by weight |
|---|---|
| HEMA | 8.0 |
| TEGDMA | 40.0 |
| BisGMA | 29.66 |
| EBPADMA | 20.0 |
| BPB | 0.5 |
| BPO | 1.70 |
| BHT | 0.14 |

C) Base and Catalyst Pastes compositions (in parts by weight)

| Ingredients | Base Paste (wt. %) | Catalyst Paste (wt %) |
|---|---|---|
| Base Resin Mixture (A) | 50.0 | — |
| Catalyst Resin Mixture (B) | — | 50.0 |
| Zinc Oxide | 10.0 | 10.0 |
| Barium Sulphate | 10.0 | 10.0 |
| BaAlBSi Filler[1] | 26.6 | 26.6 |
| OX-50[1] | 1.4 | 1.4 |
| TS-530 | 2.0 | 2.0 |

[1]Both BaAlBSi filler and OX-50 fumed silica were surface treated with γ-methacryloyloxypropyltrimethoxysilane.

The Base Paste had a consistency value of 6.1 cm and the Catalyst Paste had a consistency value of 5.6 cm. The mixed Base and Catalyst Paste had a working time of 19 min and set time of 25 min. The set material had a Shore A hardness of 98, a flexural modulus of 3900±500 MPa and a flexural strength of 104.7±5.2 MPa. Since these pastes were formulated without any elastomeric (meth)acrylate oligomers, the cured material was rather hard, which is reflected by both its much higher flexural modulus and much higher Shore A hardness value when compared with the set materials in Examples 1 and 2. Therefore, the material in this comparative example was not suitable as a root canal sealing and/or filling material because it would be extremely difficult to remove the set material from the root canal if rework was needed.

The above Examples are for illustration only and in no way limit the scope of the current invention. It should be understood that the embodiments of the present invention shown and described in the specification are only preferred embodiments of the inventor who is skilled in the art and are not limiting in any way. Therefore, various changes, modifications or alterations to these embodiments may be made or resorted to without departing from the spirit of the invention and the scope of the following claims.

What is claimed is:

1. A method of sealing and/or filling a root canal comprising preparing an endodontic sealing and/or filling composition comprising
   a) at least one elastomeric (meth)acrylate oligomer selected from the group consisting of an elastomeric urethane (meth)acrylate oligomer and an elastomeric polyalkyleneglycol (meth)acrylate oligomer;
   b) at least one diluent comonomer having at least one ethylenically unsaturated group;
   c) at least one filler; and
   d) a polymerization initiator system,
and providing said composition to said root canal.

2. The method of claim 1 wherein the elastomeric urethane (meth)acrylate oligomer is selected from the group consisting of
Structure I (Urethane Acrylate Oligomer Type 1)

$$H_2C=C(R')-C(O)-O-R^1-OCNH-R_3-NHCO-[R^3-CNH-R_4-NHCO]_x-R^4-CNH-R_5-NHCO-R^2-O-C(O)-C(R'')=CH_2$$

Structure II (Urethane Acrylate Oligomer Type 2)

$$H_2C=C(R')-C(O)-O-R_1-NHCO-R^3-CNH-[R_3-NHCO-R^4-CNH]_x-R_4-NHCO-R^5-CNH-R_2-O-C(O)-C(R'')=CH_2$$

where
$x=0-30$;
R', R''=H or $CH_3$; R' and R'' may be the same or different;
$R_1, R_2 = -C_nH_{2n}-$; $n=1-14$; $R_1$ and $R_2$ is an aliphatic group and may be the same or different;
$R_3$, $R_4$ and $R_5$ are the bivalent radicals of an organic diisocyanate compound and may be the same or different;

$R^1, R^2 = -(G-O)_y-G$; $y=0-40$; $R^1, R^2$ may be the same or different;
$R^3$, $R^4$, $R^5$ may be the same or different, and is selected from the following structures:
$-(G-O)_p-$;

$$-(G-O)_p-\left[C(O)-(CH_2)_q-O-(G-O)_p\right]_m-;$$

$$-(G-O)_p-\left[C(O)-(CH_2)_q-C(O)-O-(G-O)_p\right]_m-;$$

where p, q=1–40; m=1–30; and G in $R^1, R^2, R^3, R^4$ and $R^5$ is selected from the following structures:
$-(CH_2)_n-$;

$$-CH(CH_3)CH_2-; \quad -CH(C_2H_5)CH_2-;$$

$n=1–12$.

3. The method of claim 2 where $R_1$, $R_2$ is selected from the group consisting of $-CH_2CH_2-$, $-CH_2CH_2CH_2-$, and $-CH_2CH_2CH_2CH_2-$.

4. The method of claim 2 where $R_3$, $R_4$ and $R_5$ are the bivalent radicals of an organic diisocyanate compound selected from the group consisting of 1,4-tetramethylene diisocyanate; 1,5-pentamethylene diisocyanate; 1,6-hexamethylene diisocyanate; 1,7-heptamethylenediisocyanate; 1,8-octamethylene diisocyanate; 1,9-nonamethylene diisocyanate; 1,10-decamethylene diisocyanate; 2,4,4-trimethyl-1,6-hexamethylene diisocyanate; 2,2,4-trimethyl-1,6-hexamethylene diisocyanate; 2,2,4-trimethyl-1,5-pentamethylene diisocyanate; toluene diisocyanate; diphenylmethane-4,4'-diisocyanate; isophorone diisocyanate; dicyclohexylmethane-4,4'-diisocyanate; 1,4-cyclohexyl diisocyanate and 1,3-cyclohexyl diisocyanate.

5. The method of claim 2 where $R_3$, $R_4$ and $R_5$ are the bivalent radicals of an organic diisocyanate compound selected from the group consisting of 1,6-hexamethylene diisocyanate; 2,4,4-trimethyl-1,6-hexamethylene diisocyanate; 2,2,4-trimethyl-1,6-hexamethylene diisocyanate; toluene diisocyanate; diphenylmethane-4,4'-diisocyanate and isophorone diisocyanate.

6. The method of claim 2 wherein $R^1$ and $R^2$ are selected from the group consisting of $-CH_2CH_2-$; $-CH_2CH_2CH_2-$; $-CH(CH_3)CH_2-$; $-CH_2CH_2CH_2CH_2-$; $-CH_2CH_2OCH_2CH_2-$ and $-CH(CH_3)CH_2OCH(CH_3)CH_2-$.

7. The method of claim 1 wherein the elastomeric polyalkyleneglycol (meth)acrylate oligomer has the following structure Structure III (Polyalkyleneglycol Acrylate Oligomer)

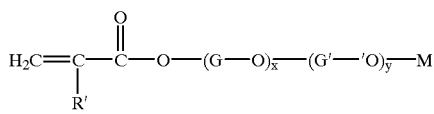

where
x=0–100; y=0–100, and x-y=6–100
R'=H or $CH_3$;
G and G' are selected from the following structures:
—$(CH_2)_m$—,

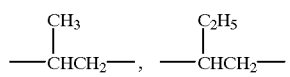

where n=1–12;
M is selected from following structures:
H, $C_nH_{2n+1}$ (alkyl group),

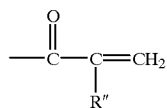

where
n=1–8;
R"=H or $CH_3$.

8. The method of claim 1 wherein the elastomeric polyalkyleneglycol (meth)acrylate oligomer is selected from the group consisting of polyethyleneglycol mono-(meth)acrylate, polyethyleneglycol di-(meth)acrylate, polyisopropyleneglycol mono-(meth)acrylate, polyisopropyleneglycol di-(meth)acrylate, polytetramethyleneglycol mono-(meth)acrylate, polytetramethyleneglycol di-(meth)acrylate.

9. The method of claim 1 wherein the ethylenically unsaturated group is selected from the group consisting of a vinyl group and a (meth)acrylate group.

10. The method of claim 1 wherein the concentration of the elastomeric (meth)acrylate oligomer is 0.5–50% by weight.

11. The method of claim 1 wherein the concentration of the elastomeric (meth)acrylate oligomer is 2–30% by weight.

12. The method of claim 1 wherein the filler is selected from the group consisting of inorganic metal, salt, inorganic oxide, silicate, aluminosilicate, aluminoborosilicate, fluoroaluminosilicate, colloidal silica, precipitated silica, polymeric solid and mixtures thereof.

13. The method of claim 1 wherein the filler contains elements selected from the group consisting of barium, zinc, silver, strontium, bismuth, tungsten, ytterbium, yttrium and mixtures thereof.

14. The method of claim 1 wherein the filler is selected from the group consisting of silver, barium sulfate strontium fluoride, barium fluoride, ytterbium fluoride, yttrium fluoride, barium tungstate, zinc oxide, bismuth(III) oxide, bismuth subcarbonate $(BiO)_2CO_3$, bariumaluminosilicate, bariumaluminoborosilicate, strontiumaluminosilicate, barium aluminofluorosilicate, strontiumaluminofluorosilicate, zincaluminosilicate and mixtures thereof.

15. The method of claim 1 wherein the initiator system is a redox initiator system comprising at least one reducing agent and at least one oxidizing agent.

16. The method of claim 15 wherein the reducing agent is selected from the group consisting of a tertiary amine, an organic compound containing the —$SO_2M$ group where M=H or alkali metal ion, ascorbic acid, and mixtures thereof.

17. The method of claim 15 wherein the reducing agent is selected from the group consisting of N,N-dihydroxyethyl p-toluidine, N,N-dimethyl p-toluidine, N,N-dimethylaminophenylethyl alcohol, N,N-dimethylaminophenylacetic acid, benzenesulfinic acid, toluenesulfinic acid, sodium benzenesulfinate, potassium benzenesulfinate, sodium toluenesulfinate and potassium toluenesulfinate.

18. The method of claim 15 wherein the oxidizing agent is an organic peroxide.

19. The method of claim 18 wherein the organic peroxide is selected from the group consisting of benzoyl peroxide, hydrogen peroxide, di-t-butyl peroxide and t-butyl hydrogen peroxide.

20. The method of claim 1 wherein the composition further comprises an antimicrobial agent.

21. The method of claim 20 wherein the antimicrobial agent is selected from the group consisting of benzalkonium chloride, iodoform, eugenol, zinc oxide, triclosan, butyl parahydroxybenzoate and mixtures thereof.

22. The method of claim 1 wherein the composition further comprises calcium hydroxide.

23. The method of claim 1 wherein the composition further comprises one or more adhesion promoters that contain at least one hydrophilic group selected from the group consisting of a hydroxyl group and an acidic group, wherein said acid group is selected from the group consisting of
—COOH;

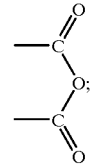

—$SO_3H$; —$SO_2H$;

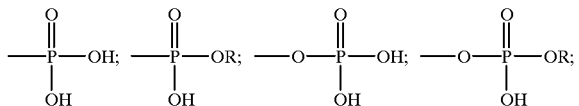

where R is an alkyl group.

24. The method of claim 23 wherein the adhesion promoter comprises at least one ethylenically unsaturated group.

25. The method of claim 23 wherein the adhesion promoter is selected from the group consisting of hydroxyethyl (meth)acrylate, glycerol di(meth)acrylate, glycerol mono (meth)acrylate, gyceryldi(meth)acrylate phosphate, (meth)acryloyloxydecyl phosphate, 4-(meth)acryloxyethyl trimellitic anhydride and mixtures thereof.

26. The method of claim 1 wherein the composition further comprises a plasticizer.

27. The method of claim 26 wherein the plasticizer is selected from the group consisting of dibutylphthalate, dibutoxyethoxyethyl adipate, dibutoxyethoxylethyl formal and mixtures thereof.

28. The method of claim 1 wherein the material further comprises at least one wetting agent or surfactant.

29. The method of claim 1 wherein the material is a two-part system selected from the group consisting of a powder/liquid two-part system and a paste/paste two-part system.

30. The method of claim 1 wherein the polymerization initiator system is a two-part redox initiator system with one part containing a reducing agent and the other part containing an oxidizing agent.

31. The method of claim 2 where G is selected from the group consisting of $-CH_2CH_2-$, $-CH_2CH_2CH_2-$, $-CH(CH_3)CH_2-$, and $-CH_2CH_2CH_2CH_2-$.

* * * * *

UNITED STATES PATENT AND TRADEMARK OFFICE
CERTIFICATE OF CORRECTION

PATENT NO. : 6,353,041 B1  
DATED : March 5, 2002  
INVENTOR(S) : Qian

It is certified that error appears in the above-identified patent and that said Letters Patent is hereby corrected as shown below:

<u>Column 15,</u>
Line 8, "(G´ — ´O)$_y$" should be -- (G´ — O)$_y$ --
Line 23, "where n= 1-12;" should be -- where m = 1-12; --;
Line 62, "barium sulfate strontium" should be -- barium sulfate, strontium --

Signed and Sealed this

Twenty-fourth Day of September, 2002

Attest:

JAMES E. ROGAN  
Attesting Officer    Director of the United States Patent and Trademark Office